United States Patent

Treuner et al.

[11] 3,960,850
[45] June 1, 1976

[54] 3-HETEROTHIO DERIVATIVES OF [(ALKOXYCARBONYL)OXYACETYL]-CEPHALOSPORINS

[75] Inventors: Uwe D. Treuner; Hermann Breuer, both of Regensburg, Germany

[73] Assignee: E. R. Squibb & Sons, Inc., Princeton, N.J.

[22] Filed: May 10, 1974

[21] Appl. No.: 468,716

[52] U.S. Cl............................. 260/243 C; 424/246
[51] Int. Cl.²...................................... C07D 501/20
[58] Field of Search............................... 260/243 C

[56] References Cited
UNITED STATES PATENTS

| | | | |
|---|---|---|---|
| 3,812,116 | 5/1974 | Takano et al. | 260/243 C |
| 3,839,329 | 10/1974 | Breuer et al. | 260/243 C |
| 3,846,418 | 11/1974 | Treuner et al. | 260/243 C |

*Primary Examiner*—Nicholas S. Rizzo
*Attorney, Agent, or Firm*—Lawrence S. Levinson; Merle J. Smith

[57] ABSTRACT

3-Heterothio derivatives of [(alkoxycarbonyl)oxyacetyl]cephalosporins which have the formula

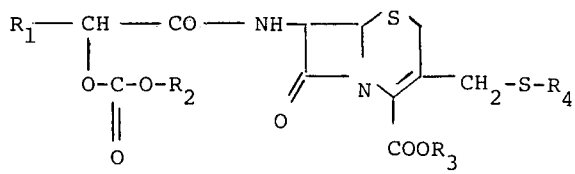

wherein $R_1$ is hydrogen, lower alkyl, phenyl, phenyl-lower alkyl or certain heterocyclic groups; $R_2$ is lower alkyl; $R_3$ is hydrogen, lower alkyl, tri(lower alkyl)silyl, tri(lowe alkyl)stannyl, a salt forming ion, or

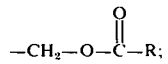

R is lower alkyl, phenyl, or phenyl-lower alkyl; $R_4$ is a five-membered nitrogen and sulfur or oxygen-containing ring system; are useful as antibacterial agents.

9 Claims, No Drawings

3-HETEROTHIO DERIVATIVES OF [(ALKOXYCARBONYL)OXYACETYL]CEPHALOSPORINS

SUMMARY OF THE INVENTION

This invention relates to new [(alkoxycarbonyl) oxyacetyl]cephalosporins of the formula (I)
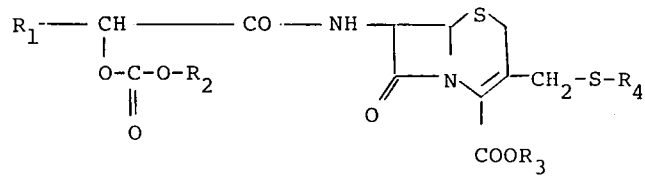

$R_1$ is a hydrogen, lower alkyl, phenyl, phenyllower alkyl, thienyl, furyl or pyridyl.

$R_3$ is hydrogen, lower alkyl, tri(lower alkyl)silyl, tri(lower alkyl)stannyl, a salt forming ion, or

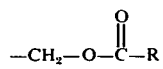

wherein R is lower alkyl, phenyl, or phenyl-lower alkyl.

$R_4$ is a five-membered nitrogen and sulfur or oxygen-containing heterocyclic group including isoxazole, isothiazole, oxadiazole, thiadiazole, tetrazole and their lower alkyl substituted analogs.

$R_2$ is lower alkyl.

DETAILED DESCRIPTION OF THE INVENTION

The various groups represented by the symbols have the meanings defined below and these definitions are retained throughout this specification.

The lower alkyl groups are straight or branched chain hydrocarbon groups containing 1 to 8 carbon atoms, preferably 1 to 4 carbons. Examples of the type of these groups are methyl, ethyl, propyl, isopropyl, butyl, t-butyl, pentyl, isopentyl, etc. The phenyl-lower alkyl groups include such lower alkyl groups attached to a phenyl, e.g., benzyl, phenethyl, etc.

The salt forming ions represented by $R_3$ are metal ions, e.g., alkali metal ions such as sodium or potassium, alkaline earth metal ions such as calcium or magnesium, or an amine salt ion, of which a number are known for this purpose, for example, lower alkylamines like methylamine or triethylamine, aralkylamines like dibenzylamine, N,N-dibenzylethylene-diamine, N-ethylpiperidine, etc.

Preferred embodiments of this invention are as follows:

$R_1$ is hydrogen, lower alkyl of 1 to 4 carbons, phenyl, benzyl, furyl, thienyl or pyridyl, especially phenyl.

$R_2$ is lower alkyl of 1 to 4 carbons, especially methyl or ethyl.

$R_3$ is hydrogen, alkali metal, trimethylsilyl or

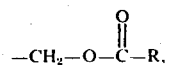

especially hydrogen, pivaloyloxymethyl, sodium or potassium. R is lower alkyl.

$R_4$ is thiadiazole, tetrazole and their methyl substituted analogs, especially, 1,3,4-thiadiazole, 5-methyl-1,3,4-thiadiazole, tetrazole and 1-methyltetrazole.

The new derivatives of [(alkoxycabonyl)oxyacetyl]-cephalosporins of this invention are produced by reacting 7-aminocephalosporanic acid (7-ACA) (or derivative wherein $R_3$ is other than hydrogen) with a mercaptan HS—$R_4$ at a pH of about 8 – 8.5 to obtain the derivative of the formula (II)
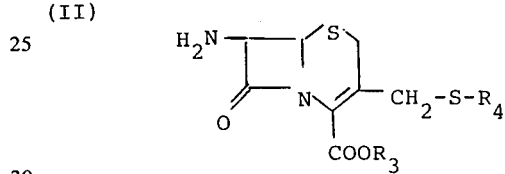

The product of formula II is then acylated on the amino group with an oxycarbonyloxyacetic acid of the formula (III)
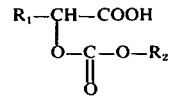

or an activated derivative of the former (II).

The activated derivatives referred to include, for example, the reaction product with an anhydride forming reagent such as ethylchloroformate, benzoyl chloride, pivaloyl chloride, etc., or with bisimidazolecarbonyl, dicyclohexylcarbodiimide, p-nitrophenol or the like.

The reaction between the 7-aminocephalosporanic acid compound and the oxycarbonyloxyacetic acid is effected, for example, by converting the latter to the acid chloride with an agent such as thionyl chloride and adding, at a low temperature, e.g., 0° C. or below, the acid chloride to a mixture of the 7-aminocephalosporanic acid and a salt forming organic base, such as triethylamine, pyridine or the like, in an inert organic solvent such as chloroform, methylene chloride, dioxane, benzene or the like. The product of the reaction is then isolated by conventional procedures, e.g., by concentration or evaporation of the solvent.

The acids of formula III are formed by reacting an acid of the formula (IV)
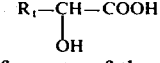

with a chloroformate of the formula (V)

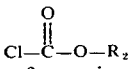

in the presence of a tertiary base such as dimethylaniline.

Alternatively, the 7-ACA can be first acylated and then the product of this reaction is made to react with the mercaptan HS—R$_4$.

Further process details are also provided in the illustrative examples.

Certain of the compounds of this invention may exist in different optically active forms. The various stereoisomeric forms as well as racemic mixtures are within the scope of the invention.

The compounds of this invention have antibacterial activity against both gram positive and gram negative organisms such as *Staphylococcus aureus*, *Proteus rettgeri* and *E. hafniae*. They may be used as antibacterial agents in a prophylactic manner, e.g., in cleaning or disinfecting compositions, or otherwise to combat infections due to organisms such as those named above, and in general may be utilized in a manner similar to cephradine and other cephalosporins. For example, a compound of formula I or a physiologically acceptable salt thereof may be used in various animal species in an amount of about 1 to 150 mg./kg. daily, orally or parenterally, in single or two to four divided doses to treat infections of bacterial origin, e.g., 4.0 mg./kg. in mice.

Oral forms give prompt high blood levels which are maintained for relatively long periods.

Up to about 600 mg. of a compound of formula I or a physiologically acceptable salt thereof can be incorporated in an oral dosage form such as tablets, capsules or elixirs or in an injectable form in a sterile aqueous vehicle prepared according to conventional pharmaceutical practice.

They are also useful in cleaning or disinfecting compositions, e.g., for cleaning barns or dairy equipment, at a concentration of about 0.01 to 1% by weight of such compounds admixed with, suspended or dissolved in conventional inert dry or aqueous carriers for application by washing or spraying. They are additionally useful as nutritional supplements in animal feeds.

The following examples are illustrative of the invention. All temperatures are on the centrigrade scale. Additional variations are produced in the same manner by appropriate substitution in the starting material.

EXAMPLE 1

DL-α-[(Methoxycarbonyl)oxy]phenylacetic acid 60 gms. (0.4 moles) of DL-mandelic acid are dissolved in 50 ml. of tetrahydrofuran. 50 gms. (0.4 moles) of dimethylaniline are added and the mixture is cooled to −20°. 45 gms. (0.5 moles) of methyl chloroformate are added with vigorous stirring. After 30 minutes, the reaction mixture is poured into 500 ml. of ice-water and extracted with ethyl acetate. The organic phase is washed with 100 ml. of 2N HCl solution and concentrated after drying over sodium sulfate. A light oil is obtained which crystallizes on standing overnight. The product, DL-α-[(methoxycarbonyl)oxy]-phenylacetic acid is recrystallized from cyclohexane to obtain white crystals, m.p. 103°–105°.

EXAMPLE 2

DL-60 -[(Ethoxycarbonyl)oxy]phenylacetic acid

DL-α-[(Ethoxycarbonyl)oxy]phenylacetic acid is obtained as a light yellow oil by the procedure of Example 1 substituting an equivalent amount of ethyl chloroformate for the methyl chloroformate.

EXAMPLE 3

DL-α-[(Methoxycarbonyl)oxy]phenylacetic acid chloride 4.20 gms. (20 mM) of DL-α-[(methoxycarbonyl)oxy]-phenylacetic acid, 3.57 gms. (30 mM) of thionyl chloride, 50 ml. of ether and a drop of dimethylformamide are stirred for 24 hours at room temperature. Evaporation of the solvent and excess thionyl chloride in an oil-pump vacuum yields 4.5 gms. of crude DL-α-[(methoxycarbonyl)oxy]phenylacetic acid chloride. This is used without further purification.

EXAMPLE 4

3-[[(5-Methyl-1,3,4-thiadiazol-2-yl)thio]methyl]-7-amino-8-oxo-5-thia-1-azabicyclo[4.2.0]oct-2-ene-2-carboxylic acid A mixture of 13.6 g. (0.5 M) of 7-aminocephalosporanic acid (7-ACA) in 100 ml. of water and 50 ml. of acetone are brought to pH 8 with sodium hydroxide while stirring. 9.8 g. (0.57 M) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 5

3-[[(3-Methyl-1,2,4-thiadiazol-5-yl)thio]methyl]-7-amino-8-oxo-5-thia-1-azabicyclo[4.2.0]oct-2-ene-2-carboxylic acid By substituting 3-methyl-1,2,4-thiadiazole-5-thiol for the 2-methyl-1,3,4-thiadiazole-5-thiol in the procedure of Example 4, 11.6 g. of 3-[[(3-methyl-1,2,4-thiadiazole-5-yl)thio]methyl]-7-amino-8-oxo-5-thia-1-azabicyclo[4.2.0]oct-2-ene-2-carboxylic acid, m.p. 186° (dec.) are obtained.

EXAMPLE 6

3[[(1-Methyl-1H-tetrazol-5-yl)thio]methyl]-7-amino-8-oxo-5-thia-1-azabicyclo[4.2.0]oct-2-ene-2-carboxylic acid By substituting 0.57 M of 1-methyl-1H-tetrazole-5-thiol for the 2-methyl-1,3,4-thiadiazole-5-thiol in the procedure of Example 4, 3-[[(1-methyl-1H-tetrazol-5-yl)thio]methyl]-7-amino-8-oxo-5-thia-1-azabicyclo[4.2.0]oct-2-ene-2-carboxylic acid is obtained.

EXAMPLE 7

DL-7β-[[2-(Methoxycarbonyl)oxy]phenylacetyl-]amino]-3-[[(1-methyl-1H-tetrazol-5-yl)thio]methyl]-8-oxo-5-thia-1-azabicyclo[4.2.0]oct-2-ene-2-carboxylic acid 6.3 gms. (20 mM) of the product of the Example 6 are suspended in 50 ml. of water/acetone (1:1) and 4 gms. (50mM) of sodium bicarbonate are added with stirring. After some time, a clear solution forms to which 4.6 gms. (20 mM) of DL-α-[(methoxycarbonyl)oxy]phenylacetic acid chloride are slowly added dropwise at a temperature of −5°. The mixture is then stirred for 1 hour at room temperature, filtered from the insoluble products and one half of the volume reduced under vacuum. The rest of the solution is washed once with ether and the ether is then evaporated. 30 ml. of ethyl acetate are added to the water phase and then acidified with 2N HCl solution at pH 2.5. The water phase is extracted once more with 20 ml. of ethyl acetate. The combined organic phases are washed with water, dried over sodium sulfate and, after removing the solvent in vacuum, 2.7 gms. of DL-7β-[[[ 2-(methoxycarbonyl)oxy]phenylacetyl]amino]-3-[[(1-methyl-1H-tetrazol-5-yl)thio]methyl]-8-oxo-5-thia-1-azabicyclo[4.2.0]oct-2-ene-2-carboxylic acid are obtained. Repeated recrystallization from $CH_2Cl_2/CCl_4$ yields 1.6 gms. of beige powder, m.p. 108° (dec.). The substance crystallizes with 1 mol. of methylene chloride. The potassium salt is obtained by freeze drying a molecular equivalent solution of the acid and potassium bicarbonate in water in the form of a light beige powder, m.p. 158° (dec.).

EXAMPLE 8

DL-7β-[[2-[(Methoxycarbonyl)oxy]phenylacetyl-]amino]-3-[[(5-methyl-1,3,4-thiadiazol-2-yl)thio]methyl]-8-oxo-5-thia-1-azabicyclo[4.2.0]oct-2-ene-2-carboxylic acid By substituting 6.5 gms. (20 mM) of 3-[[(5-methyl-1,3,4-thiadiazol-2-yl)thio]methyl]-7-amino-8-oxo-5-thia-1-azabicyclo[4.2.0]oct-2-ene-2-carboxylic acid for the starting material and reacting this with 4.5 gms. of DL-2-[(methoxycarbonyl)oxy]phenylacetic acid chloride according to the procedure of Example 7, there are obtained 3.3 gms. of DL-7β-[[2-[(methoxycarbonyl)oxy]phenylacetyl]-amino]-3-[[(5-methyl-1,3,4-thiadiazol-2-yl)thio]methyl]-8-oxo-5-thia-1-azabicyclo[4.2.0]oct-2-ene-2-carboxylic acid as a beige powder. After recrystallization with chloroform/ether, the yield is 2.5 gms, m.p. 130° (dec.). Potassium salt;m.p. 155° (dec.).

EXAMPLE 9

Alternate route for the preparation of:
DL-7β-[[2-[(Methoxycarbonyl)oxy]phenylacetyl-]amino]-3-[[(5-methyl-1,3,4-thiadiazol-2-yl)thio]methyl]-8-oxo-5-thia-1-azabicyclo[4.2.0]oct-2-ene-2-carboxylic acid 1.95 gms. (10 mM) of DL-α-[(methoxycarbonyl)oxy]phenylacetic acid are dissolved in 25 ml. of dimethylformamide at 0° and 2.01 gms. (10 mM) of dicyclohexylcarbodiimide are added. After stirring for 1 hour, a solution of 3.5 gms. (10 mM) of 3-[[(5-methyl-1,3,4-thiadiazol-2-yl)thio]methyl]-7-amino-8-oxo-5-thia-1-azabicyclo[4.2.0]oct-2-ene-2-carboxylic acid and 2 gms. (20 mM) of triethylamine is added to 50 ml. of dimethylformamide. After stirring for 24 hours at 0°–5°, the dicyclohexylurea which forms is filtered off and the solvent distilled off at 50° in vacuum. The residue is extracted with ethyl acetate, the ethyl acetate solution is filtered over charcoal and after treating with petroleum ether/ether, 0.9 gms. of DL-7β-[[[2-[(methoxycarbonyl)oxy]-phenylacetyl]amino]-3-[[(5-methyl-1,3,4-thiadiazol-2-yl)thio]-methyl]-8-oxo-5-thia-1-azabicyclo[4.2.0]oct-2-ene-carboxylic acid is obtained in the form of a light beige powder, m.p. 127° (dec.).

EXAMPLE 10

Alternate route for the preparation of:
DL-7β-[[2-[(Methoxycarbonyl)oxy]phenylacetyl-]amino]-3-[[(1-methyl-1H-tetrazol-5-yl)thio]methyl]oxo-5-thia-1-azabicyclo[4.2.0]oct-2-ene-2-carboxylic acid a.

DL-7β-[[2-[(Methoxycarbonyl)oxy]-phenylacetylamino]-3-(hydroxymethyl)-8-oxo-5-thia--1-azabicyclo[4.2.0]oct-2-ene-2--carboxylic acid, 3-acetate 38.5 gms. (0.02 moles) of the product of Example 3 is added dropwise at −28° to a mixture of 5.4 gms. (0.02 moles) of 7-aminocephalosporanic acid and 4 gms. (0.04 moles) of triethylamine in 100 ml. of chloroform. After 1.2 hour., 50 ml. of 2N HCl are added. The organic phase is washed with water, dried over sodium sulfate and concentrated. After crystallization from methylene chloridechloroform, 1 gram of light yellow DL-7β-[[2-[(methoxycarbonyl)oxy]phenyl-]acetylamino]-3-(hydroxymethyl)-8-oxo-5-thia-1-azabicyclo[4.2.0]oct-2-ene-2-carboxylic acid, 3-acetate is obtained, m.p. 80°. The potassium salt melts at 152°.

b.

DL-7β-[[[2-[(methoxycarbonyl)oxy]phenylacetyl-]amino]-3-[[(1-methyl-1H-tetrazol-5yl)thio]methyl]oxo-5-thia-1-azabicyclo[[4.2.0]oct-2-ene2-carboxylic acid 2.32 gms. 5 mM) of DL-7β-[[[2-[(methoxycabonyl)oxy]phenylacetyl]amino]-3-(hydroxymethyl)-8-oxo-5-thia-1-azabicyclo[4.2.0]oct-2-ene-2-carboxylic acid, 3-acetate are dissolved in acetone/water (1:1 ).

0.6 gms. (5.1 mM) of 1-methyl-1H-tetrazole-5-thiol are added and the pH is adjusted to 7.8 with sodium carbonate. The mixture is then heated for 6 hours at 60° and the pH held constant by repeated additions of sodium carbonate. After cooling, the acetone is distilled off in vacuum and the remaining solution is extracted with 20 ml. of ethyl acetate. The water phase is then brought to a pH value of 2.5 with 2N HCl. The precipitate which forms is filtered off and recrystallized with methylene chloride, yield: 0.3 gm. of pure DL-7β-[[[2-[(methoxycarbonyl)oxy]phenylacetyl]amino]-3-[[(1-methyl-1H-tetrazol-5-yl)thio]methyl]oxo-5-thia-1-azabicyclo[4.2.0]oct-2-ene-2-carboxylic acid, m.p. 102° (dec.).

EXAMPLE 11

DL-7β-[[[2-[(Ethoxycarbonyl)oxy]-2-phenylacetyl]amino]-3-(hydroxymethyl)-8-oxo-5-thia-1-azabicyclo[4.2.0]oct-2-ene-carboxylic acid, 3 acetate DL-7β-[[[2-[(Ethoxycarbonyl)oxy]-2-phenylacetyl]amino]-3-(hydroxymethyl)-8-oxo-5-thia-1-azabicyclo[4.2.0]oct-2-ene-carboxylic acid, 3 acetate is obtained by the procedure of Example 10a by substituting an equivalent amount of DL-α-[(ethoxycarbonyl)oxy]phenylacetic acid chloride for the DL-[(methoxycarbonyl)oxy]phenylacetic acid chloride, m.p. 79° (dec.). The potassium salt melts at 143° (dec.).

EXAMPLES 12 – 38

The products below are obtained by the procedure of Example 7 by reacting the acid chloride

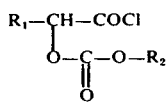

with one of the following:
3-[[(5-methyl-1,3,4-thiadiazolyl-2-yl)thio]-methyl]-7-amino-8-oxo-5-thia-1-azabicyclo[4.2.0]oct-2-ene-2-carboxylic acid.
3-[[(1-methyl-1H-tetrazol-5-yl)thio]methyl]-7-ACA
3-[[(3-isothiazolyl)thio]methyl]-7-ACA
3-[[(1,3,4-oxadiazol-2-yl)thio]methyl]-7-ACA
3-[[(5-ethyl-1,3,4-oxadiazol-2-yl)thio]methyl]-7-ACA
3-[[(1,2,3,4-tetrazol-5-yl)thio]methyl]-7-ACA
3-[[(1-ethyl-1H-tetrazol-5-yl)thio]methyl]-7-ACA
3-[[(3-methyl-5-isothiazolyl)thio]methyl]-7-ACA
3-[[3-isoxazolyl)thio]methyl]-7-ACA
3-[[(5-methyl-3-isoxazolyl)thio]methyl]-7-ACA
3-[[(1,2,4-thiadiazol-3yl)thio]methyl]-7-ACA
3-[[(5-butyl-1,2,4-thiadiazol-3-yl)thio]methyl]-7-ACA
3-[[(5-ethyl-3-isoxazolyl)thio]methyl]-7-ACA
3-[[(3-methyl-4-isoxazolyl)thio]methyl]-7-ACA
3-[[(3-methyl-1,2,4-oxadiazol-5-yl)thio]methyl]-7-ACA
3-[[(5-ethyl-3-isothiazolyl)thio]methyl]-7-ACA
3-[[(1,2,4-thiadiazol-5-yl)thio]methyl]-7-ACA

| Example | |
|---|---|
| 12 | DL-7β-[[[2-(methoxycarbonyl]oxy]-2-(2-pyridyl)-acetyl]amino]-3-[[(1,3,4-thiadiazol-2-yl)thio]methyl-8-oxo-5-thia-1-azabicyclo[4.2.0]oct-2-ene-2-carboxylic acid |
| 13 | DL-7β-[[[2-(n-butoxy)carbonyl]oxy]-2-phenylacetyl]-amino]-3-[[(1,3,4-oxadiazol-2-yl)thio]methyl]-8-oxo-5-thia-1-azabicyclo[4.2.0]oct-2-ene-2-carboxylic acid |
| 14 | DL-7β-[[[2-ethoxy)carbonyl]oxy]-2-benzylacetyl]-amino]-3-[[5-ethyl-1,3,4-oxadiazol-2-yl)thio]-methyl]-8-oxo-5-thia-1-azabicyclo[4.2.0]oct-2-ene-2-carboxylic acid |
| 15 | DL-7β-[[[2-(methoxy)carbonyl]oxy]acetyl]amino]--3-[[(3-methyl-5-isothiazolyl)thio]methyl]-8-oxo 5-thia-1-azabicyclo[4.2.0]oct-2-ene-2-carboxylic acid |
| 16 | DL-7β-[[(2-ethoxy)carbonyl]oxy]-2-(2-thienyl)-acetyl]amino]-3-[[(3-isothiazolyl)thio]methyl]-8-oxo-5-thia-1-azabicyclo[4.2.0]oct-2-ene-2-carboxylic acid. |
| 17 | DL-7β-[[[2-methoxycarbonyl]oxy]-2-phenylacetyl]-amino]-3-[[(3-isoxazolyl)thio]methyl]-8-oxo-5-thia-1-azabicyclo[4.2.0]oct-2-ene-2-carboxylic acid |
| 18 | DL-7β-[[[2-(methoxy)carbonyl]oxy]-2-phenylacetyl]-amino]-3-[[(5-methyl-3-isoxazolyl)thio]methyl]-8-oxo-5-thia-1-azabicyclo[4.2.0]oct-2-ene-2-carboxylic acid |
| 19 | DL-7β-[[[2-(propoxy)carbonyl]oxy]-2-phenylacetyl]-amino]-3-[[(1,2,4-thiadiazol-5-yl)thio]methyl]-8-oxo-5-thia-1-azabicyclo[4.2.0]oct-2-ene-2-carboxylic acid |
| 20 | DL-7β-[[[2-(methoxy)carbonyl]oxy]acetyl]amino]-3-[[ (1,2,4-thiadiazol-3-yl)thio]methyl]-8-oxo-5-thia-1-azabicyclo[4.2.0]oct-2-ene-2-carboxylic acid |
| 21 | DL-7β-[[[2-(methoxy)carbonyl]oxy]-2-phenylacetyl]-amino]-3-[[(5-butyl-1,2,4-thiadiazol-3-yl)thio]-methyl]-8-oxo-5-thia-1-azabicyclo[4.2.0]oct-2-ene-2-carboxylic acid |
| 22 | DL-7β-[[2-(methoxy)carbonyl]oxy]butyramido]-3-[[(1,2,3,4-tetrazol-5-yl)thio]methyl]-8-oxo-5-thia-1-azabicyclo[4.2.0]oct-2-ene-2-carboxylic acid |
| 23 | DL-7β-[[(2-methoxy)carbonyl]oxy]propionamido]-3-[[(5-methyl-3-isothiazolyl)thio]methyl]-8-oxo-5-thia-1-azabicyclo[4.2.0]oct-2-ene-2-carboxylic acid |
| 24 | DL-7β-[[[2-methoxy)carbonyl]oxy]-2-phenylacetyl]-amino]-3-[[(3-isoxazoly)thio]methyl]-8-oxo-5-thia-1-azabicyclo[4.3.0]oct-2-ene-2-carboxylic acid |
| 25 | DL-7β-[[[2-(butoxy)carbonyl]oxy]-2-phenylacetyl]-amino]-3-[[(3-methyl-4-isoxazolyl)thio]methyl]-8-oxo-5-thia-1-azabicyclo[4.2.0]oct-2-ene-2-carboxylic acid |
| 26 | DL-7β-[[[2-(methoxy)carbonyl]oxy]-2-phenylacetyl]-amino]-3-[[(3-methyl-1,2,4-oxadiazol-5-yl)thio]methyl]- |

| Example | |
|---|---|
| | 8-oxo-5-thia-1-azabicylco[4.2.0]oct-2-ene-2-carboxylic acid |
| 27 | DL-7β-[[[2-(methoxy)carbonyl]oxy]acetyl]amino]-3-[[(1-ethyl-1H-tetrazol-5-yl)thio]methyl]-8-oxo-5-thia-1-azabicyclo[4.2.0]oct-2-ene-2-carboxylic acid |
| 28 | DL-7β-[[[2-(methoxy)carbonyl]oxy]-2-phenylacetyl]-amino]-3-[[(1-ethyl-1H-tetrazol-5-yl)thio]methyl]-8-oxo-5-thia-1-azabicyclo[4.2.0]oct-2-ene-2-carboxylic acid |
| 29 | DL-7β-[[[2-(ethoxy)carbonyl]oxy]-2-phenylacetyl]-amino]-3-[[3-thiazolyl]thio]methyl]-8-oxo-5-thia-1-azabicyclo[4.2.0]oct-2-ene-2-carboxylic acid |
| 30 | DL-7β-[[[2-(methoxy)carbonyl]oxy]-2-phenylacetyl]-amino]-3-[[(2-methyl-1,3,4-thiadiazol-5-yl)thio]-methyl]-8-oxo-5-thia-1-azabicyclo[4.2.0]oct-2-ene-2-carboxylic acid |
| 31 | DL-7β-[[[2-(ethoxy)carbonyl]oxy]-2-(2-furyl)-acetyl]-amino]-3-[[(5-methyl-1,3,4-thiadiazol-2-yl)thio]-methyl]-8-oxo-5-thia-1-azabicyclo[4.2.0]oct-2-ene-2-carboxylic acid and potassium salt |
| 32 | DL-7β-[[[2-(propoxy)carbonyl]oxy]-2-(2-thienyl)-acetyl]amino]-3-[[(1,3,4-oxadiazol-2-yl)thio]-methyl]-8-oxo-5-thia-1-azabicyclo[4.2.0]oct-2-ene-2-carboxylic acid and sodium salt |
| 33 | DL-7β-[[[(2-ethoxy)carbonyl]oxy]acetyl]amino]-3-[[(5-ethyl-1,3,4-oxadiazol-2-yl)thio]methyl]-8-oxo-5-thia-1-azabicyclo[4.2.0]oct-2-ene-2-carboxylic acid |
| 34 | DL-7β-[[[2-(n-butoxy)carbonyl]oxy]acetyl]amino-3-[[(1,2,3,4-tetrazol-5-yl)thio]methyl]-8-oxo-5-thia-1-azabicyclo[4.2.0]oct-2-ene-2-carboxylic acid |
| 35 | DL-7β-[[[2-(methoxy)carbonyl]oxy]-2-(2-thienyl)acetyl]amino]-3-[[(2-methylthiazol-5-yl)thio]-methyl-8-oxo-5-thia-1-azabicyclo[4.2.0]oct-2-ene-2-carboxylic acid triethylamine salt |
| 36 | DL-7β-[[[2-(ethoxy)carbonyl]oxy]-2-(3-furyl)acetyl]-amino]-3-[[(1,2,4-thiadiazol-3-yl)thio]methyl]-8-oxo-5-thia-1-azabicyclo[4.2.0]oct-2-ene-2-carboxylic acid pivaloyloxymethyl ester |
| 37 | DL-7β-[[[2-(methoxy)carbonyl]oxy]-2-(3-pyridyl)-acetyl]amino]-3-[[(3-isoxazolyl)thio]methyl]-8-oxo-5-thia-1-azabicyclo[4.2.0]oct-2-ene-2-carboxylic acid trimethylsilyl ester |
| 38 | DL-7β-[[[2-(methoxy)carbonyl]oxy]-2-(2-thienyl)acetyl]-amino]-3-[[(1,3,4-oxadiazol-2-yl)thio]methyl]-8-oxo-5-thia-1-azabicyclo[4.2.0]oct-2-ene-2-carboxylic acid |

What is claimed is:
1. A compound of the formula

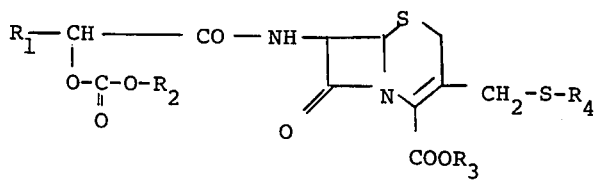

wherein
$R_1$ is phenyl or pyridyl;
$R_2$ is lower alkyl;
$R_3$ is hydrogen, lower alkyl, tri(lower alkyl)silyl, tri(lower alkyl)stannyl, alkali metal, alkaline earth metal or (lower alkyl)amine;
$R_4$ is isoxazole, isothiazole, oxadiazole, thiadiazole, tetrazole and their lower alkyl derivatives.

2. A compound as in claim 1 wherein $R_1$ is phenyl.
3. A compound as in claim 1 wherein $R_1$ is phenyl, $R_2$ is lower alkyl, $R_3$ is hydrogen and $R_4$ is (lower alkyl)tetrazole.
4. A compound as in claim 3 wherein each lower alkyl group is methyl.
5. A compound as in claim 1 wherein $R_1$ is phenyl, $R_2$ is lower alkyl, $R_3$ is hydrogen and $R_4$ is (lower alkyl)thiadiazole.
6. A compound as in claim 5 wherein $R_2$ is methyl and $R_4$ is 5-methyl-1,3,4-thiadiazole.
7. Alkali metal salt of the compound of claim 6.
8. A salt as in claim 7 wherein the alkali metal is potassium.
9. A compound as in claim 1 wherein $R_1$ is phenyl, $R_2$ is methyl, $R_3$ is potassium and $R_4$ is 1-methyl-1H-tetrazol-5-yl.

* * * * *